(12) United States Patent
Castro

(10) Patent No.: US 12,279,774 B2
(45) Date of Patent: Apr. 22, 2025

(54) CLIP APPLIER WITH STABILIZING MEMBER

(71) Applicant: TELEFLEX MEDICAL INCORPORATED, Morrisville, NC (US)

(72) Inventor: Salvatore Castro, Raleigh, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 823 days.

(21) Appl. No.: 17/213,524

(22) Filed: Mar. 26, 2021

(65) Prior Publication Data

US 2021/0212689 A1 Jul. 15, 2021

Related U.S. Application Data

(63) Continuation of application No. PCT/US2019/053145, filed on Sep. 26, 2019.
(Continued)

(51) Int. Cl.
*A61B 17/10* (2006.01)
*A61B 17/122* (2006.01)
(Continued)

(52) U.S. Cl.
CPC ............ *A61B 17/10* (2013.01); *A61B 17/122* (2013.01); *A61B 17/128* (2013.01); *A61B 17/1285* (2013.01); *A61B 2017/00367* (2013.01)

(58) Field of Classification Search
CPC ...... A61B 17/122–1285; A61B 17/064; A61B 17/068; A61B 2017/0688; A61B 17/3201;
(Continued)

(56) References Cited

U.S. PATENT DOCUMENTS 929,868 A 8/1909 Mueller
1,482,290 A 1/1924 Elzi
(Continued)

FOREIGN PATENT DOCUMENTS

AU 676836 B2 3/1997
CN 1356092 A 7/2002
(Continued)

OTHER PUBLICATIONS

International Preliminary Report on Patentability and Written Opinion issued in PCT/US2019/042390, dated Jan. 28, 2021.
(Continued)

*Primary Examiner* — Brigid K Byrd
(74) *Attorney, Agent, or Firm* — BakerHostetler

(57) ABSTRACT

A clip applier may be configured to apply a surgical clip. The clip applier may include first and second jaw members configured to engage the surgical clip, an actuating member configured to pivot at least one of the first and second jaw members between an open configuration and a closed configuration, and a stabilizing member configured to engage the surgical clip. The stabilizing member may be configured to move longitudinally with respect to the clip applier from a distal position at least partially between the first and second jaw members to a proximal position at least partially between the first and second jaw members. Movement of the stabilizing member between the distal position and the proximal position may be actuated by at least one of the first jaw member, the second jaw member, and the actuating member.

21 Claims, 5 Drawing Sheets

Related U.S. Application Data

(60) Provisional application No. 62/737,043, filed on Sep. 26, 2018.

(51) Int. Cl.
*A61B 17/128* (2006.01)
*A61B 17/00* (2006.01)

(58) Field of Classification Search
CPC ....... A61B 17/083; A61B 17/10; A61B 17/12; A61B 2017/00367
See application file for complete search history.

(56) References Cited

U.S. PATENT DOCUMENTS

| | | |
|---|---|---|
| 1,728,322 A | 9/1929 | Badrian |
| 2,384,697 A | 9/1945 | Riccardi |
| 2,594,102 A | 4/1952 | Vollmer |
| 2,598,901 A | 6/1952 | Garland |
| 2,626,608 A | 1/1953 | Garland |
| 2,635,238 A | 4/1953 | Garland |
| 2,744,251 A | 5/1956 | Vollmer |
| 2,813,269 A | 11/1957 | Jacobs |
| 2,814,222 A | 11/1957 | Sanders |
| 2,881,762 A | 4/1959 | Lowrie |
| 2,890,519 A | 6/1959 | Storz, Jr. |
| 3,032,039 A | 5/1962 | Beaty |
| 3,150,379 A | 9/1964 | Brown |
| 3,172,133 A | 3/1965 | Rizzo |
| 3,351,191 A | 11/1967 | Mallina |
| 3,446,212 A | 5/1969 | Le Roy |
| 3,463,156 A | 8/1969 | McDermott et al. |
| 3,503,396 A | 3/1970 | Pierie et al. |
| 3,503,397 A | 3/1970 | Fogarty et al. |
| 3,503,398 A | 3/1970 | Fogarty et al. |
| 3,713,533 A | 1/1973 | Reimels |
| 3,766,925 A | 10/1973 | Rubricius |
| 3,825,012 A | 7/1974 | Nicoll |
| 3,827,438 A | 8/1974 | Kees |
| 3,867,944 A | 2/1975 | Samuels |
| 3,874,042 A | 4/1975 | Eddleman et al. |
| 3,954,108 A | 5/1976 | Davis |
| 4,076,120 A | 2/1978 | Carroll et al. |
| 4,120,302 A | 10/1978 | Ziegler |
| 4,274,415 A | 6/1981 | Kanamoto et al. |
| 4,316,468 A | 2/1982 | Klieman et al. |
| 4,325,376 A | 4/1982 | Klieman et al. |
| 4,337,774 A | 7/1982 | Perlin |
| 4,344,531 A | 8/1982 | Giersch |
| 4,345,600 A | 8/1982 | Rothfuss |
| 4,346,869 A | 8/1982 | MacNeill |
| 4,390,019 A | 6/1983 | Leveen et al. |
| 4,394,864 A | 7/1983 | Sandhaus |
| 4,414,721 A | 11/1983 | Hufnagel |
| 4,418,694 A | 12/1983 | Beroff et al. |
| 4,428,374 A | 1/1984 | Auburn |
| 4,444,187 A | 4/1984 | Perlin |
| 4,450,840 A | 5/1984 | Mericle et al. |
| 4,458,682 A | 7/1984 | Cerwin |
| 4,471,780 A | 9/1984 | Menges et al. |
| 4,476,865 A | 10/1984 | Failla et al. |
| 4,487,204 A | 12/1984 | Hrouda |
| 4,487,205 A | 12/1984 | Di et al. |
| 4,492,232 A | 1/1985 | Green |
| 4,509,517 A | 4/1985 | Zibelin |
| 4,519,392 A | 5/1985 | Lingua |
| 4,527,562 A | 7/1985 | Mericle |
| 4,534,351 A | 8/1985 | Rothfuss et al. |
| 4,550,729 A | 11/1985 | Cerwin et al. |
| 4,570,633 A | 2/1986 | Golden |
| 4,579,118 A | 4/1986 | Failla |
| 4,588,160 A | 5/1986 | Flynn et al. |
| 4,589,626 A | 5/1986 | Kurtz et al. |
| 4,616,651 A | 10/1986 | Golden |
| 4,638,804 A | 1/1987 | Jewusiak |
| 4,671,281 A | 6/1987 | Beroff et al. |
| 4,686,983 A | 8/1987 | Leisman et al. |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,090 A | 5/1989 | Moore |
| 4,834,096 A | 5/1989 | Oh et al. |
| 4,854,317 A | 8/1989 | Braun |
| 4,870,965 A | 10/1989 | Jahanger |
| 4,919,152 A | 4/1990 | Ger |
| 4,924,864 A | 5/1990 | Danzig |
| 4,934,364 A | 6/1990 | Green |
| 4,936,447 A | 6/1990 | Peiffer |
| 4,938,764 A | 7/1990 | Glaberson |
| 4,938,765 A | 7/1990 | Rasmusson |
| 4,942,886 A | 7/1990 | Timmons |
| 4,950,275 A | 8/1990 | Donini |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,053,045 A | 10/1991 | Schmidt et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,141,514 A | 8/1992 | Van Amelsfort |
| 5,160,339 A | 11/1992 | Chen et al. |
| 5,163,945 A | 11/1992 | Ortiz et al. |
| 5,171,251 A | 12/1992 | Bregen et al. |
| 5,171,252 A | 12/1992 | Friedland |
| 5,172,700 A | 12/1992 | Bencini et al. |
| 5,201,416 A | 4/1993 | Taylor |
| 5,207,692 A | 5/1993 | Kraus et al. |
| 5,234,449 A | 8/1993 | Bruker et al. |
| 5,246,450 A | 9/1993 | Thornton et al. |
| 5,259,405 A | 11/1993 | Hua-Chou |
| 5,279,416 A | 1/1994 | Malec et al. |
| 5,318,589 A | 6/1994 | Lichtman |
| 5,330,442 A | 7/1994 | Green et al. |
| 5,330,487 A | 7/1994 | Thornton et al. |
| 5,366,458 A | 11/1994 | Korthoff et al. |
| 5,405,344 A | 4/1995 | Williamson et al. |
| 5,431,668 A | 7/1995 | Burbank et al. |
| 5,462,555 A | 10/1995 | Bolanos et al. |
| 5,464,416 A | 11/1995 | Steckel |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,569,274 A | 10/1996 | Rapacki et al. |
| 5,575,796 A | 11/1996 | King et al. |
| 5,575,802 A | 11/1996 | McQuilkin et al. |
| 5,591,178 A | 1/1997 | Green et al. |
| 5,607,436 A | 3/1997 | Pratt et al. |
| 5,626,585 A | 5/1997 | Mittelstadt et al. |
| 5,667,516 A | 9/1997 | Allen |
| 5,697,938 A | 12/1997 | Jensen et al. |
| 5,700,270 A * | 12/1997 | Peyser ............... A61B 17/1285 606/143 |
| 5,713,911 A | 2/1998 | Racenet et al. |
| 5,713,912 A | 2/1998 | Porter |
| 5,722,982 A | 3/1998 | Ferreira et al. |
| 5,725,538 A | 3/1998 | Green et al. |
| 5,725,542 A | 3/1998 | Yoon |
| 5,797,922 A | 8/1998 | Hessel et al. |
| 5,810,853 A | 9/1998 | Yoon |
| 5,833,696 A | 11/1998 | Whitfield et al. |
| 5,843,097 A | 12/1998 | Mayenberger et al. |
| 5,846,255 A | 12/1998 | Casey |
| 5,908,430 A | 6/1999 | Appleby |

(56) References Cited

U.S. PATENT DOCUMENTS

| | | |
|---|---|---|
| 5,921,991 A | 7/1999 | Whitehead et al. |
| 5,925,052 A | 7/1999 | Simmons |
| 5,954,731 A | 9/1999 | Yoon |
| 5,972,003 A | 10/1999 | Rousseau et al. |
| 5,976,161 A | 11/1999 | Kirsch et al. |
| 5,997,548 A | 12/1999 | Jahanger |
| 6,010,516 A | 1/2000 | Hulka |
| 6,013,088 A | 1/2000 | Karavidas |
| 6,015,417 A | 1/2000 | Reynolds, Jr. |
| 6,050,996 A | 4/2000 | Schmaltz et al. |
| 6,131,576 A | 10/2000 | Davis |
| 6,158,583 A | 12/2000 | Forster |
| 6,210,419 B1 | 4/2001 | Mayenberger et al. |
| 6,217,590 B1 | 4/2001 | Levinson |
| 6,228,104 B1 | 5/2001 | Fogarty et al. |
| 6,258,105 B1 | 7/2001 | Hart et al. |
| 6,261,303 B1 | 7/2001 | Mayenberger et al. |
| 6,273,253 B1 | 8/2001 | Forster et al. |
| 6,273,887 B1 | 8/2001 | Yamauchi et al. |
| 6,273,902 B1 | 8/2001 | Fogarty et al. |
| 6,277,117 B1 | 8/2001 | Tetzlaff et al. |
| 6,349,727 B1 | 2/2002 | Stewart, Jr. |
| 6,352,541 B1 | 3/2002 | Kienzle et al. |
| 6,387,112 B1 | 5/2002 | Fogarty et al. |
| 6,391,035 B1 | 5/2002 | Appleby et al. |
| 6,419,682 B1 | 7/2002 | Appleby et al. |
| 6,537,289 B1 | 3/2003 | Kayan et al. |
| 6,558,408 B1 | 5/2003 | Fogarty et al. |
| 6,599,298 B1 * | 7/2003 | Forster ............... A61B 17/128 606/139 |
| 6,610,073 B1 | 8/2003 | Levinson |
| 6,695,854 B1 | 2/2004 | Kayan et al. |
| 6,699,258 B1 | 3/2004 | Sadler et al. |
| 6,719,766 B1 | 4/2004 | Buelna et al. |
| 6,773,438 B1 | 8/2004 | Knodel et al. |
| 6,780,195 B2 | 8/2004 | Porat |
| 6,814,742 B2 | 11/2004 | Kimura et al. |
| 6,824,547 B2 | 11/2004 | Wilson et al. |
| 6,837,895 B2 | 1/2005 | Mayenberger |
| 6,843,253 B2 | 1/2005 | Parkes |
| 6,863,675 B2 | 3/2005 | Wilson, Jr. |
| 6,880,699 B2 | 4/2005 | Gallagher |
| 6,926,712 B2 | 8/2005 | Phan |
| 6,932,816 B2 | 8/2005 | Phan |
| 6,989,017 B2 | 1/2006 | Howell et al. |
| 7,001,412 B2 | 2/2006 | Gallagher et al. |
| 7,052,504 B2 | 5/2006 | Hughett |
| 7,094,245 B2 | 8/2006 | Adams et al. |
| 7,108,699 B2 | 9/2006 | Kobayashi |
| 7,131,977 B2 | 11/2006 | Fowler |
| 7,179,265 B2 | 2/2007 | Manetakis et al. |
| 7,194,245 B2 | 3/2007 | Furusawa et al. |
| 7,211,091 B2 | 5/2007 | Fowler et al. |
| 7,211,092 B2 | 5/2007 | Hughett |
| 7,261,724 B2 | 8/2007 | Molitor et al. |
| 7,316,696 B2 | 1/2008 | Wilson et al. |
| 7,326,223 B2 | 2/2008 | Wilson, Jr. |
| 7,329,266 B2 | 2/2008 | Royse et al. |
| 7,357,805 B2 | 4/2008 | Masuda et al. |
| 7,402,164 B2 | 7/2008 | Watson et al. |
| 7,572,266 B2 | 8/2009 | Young et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,648,514 B1 * | 1/2010 | Nakao ............... A61B 17/064 606/151 |
| 7,727,231 B2 | 6/2010 | Swanson |
| 7,753,908 B2 | 7/2010 | Swanson |
| 7,785,324 B2 | 8/2010 | Eberl |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,142,451 B2 | 3/2012 | Boulnois et al. |
| 8,262,639 B2 | 9/2012 | Mathias |
| 8,312,992 B2 | 11/2012 | Disch |
| 8,403,138 B2 | 3/2013 | Weisshaupt et al. |
| 8,425,412 B2 | 4/2013 | Rucker |
| 8,465,507 B2 | 6/2013 | Cosgrove et al. |
| 8,512,357 B2 | 8/2013 | Viola |
| 8,585,718 B2 | 11/2013 | Disch et al. |
| 8,764,774 B2 | 7/2014 | Sigmon, Jr. |
| 8,839,954 B2 | 9/2014 | Disch |
| 8,852,216 B2 | 10/2014 | Cropper et al. |
| 8,894,666 B2 | 11/2014 | Schulz et al. |
| 8,900,253 B2 | 12/2014 | Aranyi et al. |
| 8,945,151 B2 | 2/2015 | Salas |
| 8,992,566 B2 | 3/2015 | Baldwin |
| 9,084,596 B2 | 7/2015 | Stanley et al. |
| 9,119,627 B2 | 9/2015 | Cosgrove et al. |
| 9,220,507 B1 | 12/2015 | Patel et al. |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,498,241 B2 | 11/2016 | Leonhard et al. |
| 9,737,309 B1 | 8/2017 | Ad |
| 9,775,635 B2 | 10/2017 | Takei |
| 9,855,053 B2 | 1/2018 | Bagaoisan et al. |
| 9,901,352 B2 | 2/2018 | Fago et al. |
| 9,955,977 B2 | 5/2018 | Martinez et al. |
| 10,064,623 B2 | 9/2018 | Soutorine et al. |
| 10,136,898 B2 | 11/2018 | Schmidt et al. |
| 10,285,712 B2 | 5/2019 | Cosgrove et al. |
| 10,292,712 B2 | 5/2019 | Shankarsetty |
| 10,297,212 B2 | 5/2019 | Sako et al. |
| 10,307,166 B2 | 6/2019 | Willett et al. |
| 10,383,637 B2 | 8/2019 | Castro |
| 10,548,609 B2 | 2/2020 | Ramsey et al. |
| 10,758,243 B2 | 9/2020 | Salas |
| 10,925,616 B2 | 2/2021 | Shellenberger et al. |
| 11,160,550 B2 | 11/2021 | Harris et al. |
| 11,160,559 B2 | 11/2021 | Shellenberger |
| 11,266,408 B2 | 3/2022 | Shellenberger |
| 11,534,177 B2 | 12/2022 | Shellenberger et al. |
| 11,576,680 B2 | 2/2023 | Ramsey et al. |
| 11,607,227 B2 | 3/2023 | Shellenberger |
| 11,883,034 B2 | 1/2024 | Enniss |
| 2002/0046961 A1 | 4/2002 | Levinson et al. |
| 2002/0068946 A1 | 6/2002 | Kortenbach et al. |
| 2002/0111640 A1 | 8/2002 | Krause et al. |
| 2002/0169459 A1 | 11/2002 | Porat |
| 2003/0014060 A1 | 1/2003 | Wilson et al. |
| 2003/0074009 A1 | 4/2003 | Ramsey et al. |
| 2003/0158548 A1 | 8/2003 | Phan et al. |
| 2004/0010272 A1 | 1/2004 | Manetakis et al. |
| 2004/0040875 A1 | 3/2004 | Gallagher |
| 2004/0044352 A1 | 3/2004 | Fowler et al. |
| 2004/0059359 A1 | 3/2004 | Wilson |
| 2004/0097970 A1 | 5/2004 | Hughett |
| 2004/0172043 A1 | 9/2004 | Watson et al. |
| 2005/0090838 A1 | 4/2005 | Sixto et al. |
| 2005/0149063 A1 | 7/2005 | Young et al. |
| 2005/0149068 A1 | 7/2005 | Williams et al. |
| 2005/0149069 A1 | 7/2005 | Bertolero et al. |
| 2005/0165421 A1 | 7/2005 | Wilson et al. |
| 2005/0165422 A1 | 7/2005 | Wilson |
| 2005/0165423 A1 | 7/2005 | Gallagher et al. |
| 2005/0165429 A1 | 7/2005 | Douglas et al. |
| 2005/0171560 A1 | 8/2005 | Hughett |
| 2005/0234478 A1 | 10/2005 | Wixey et al. |
| 2005/0240219 A1 | 10/2005 | Kahle et al. |
| 2005/0277959 A1 | 12/2005 | Cosgrove et al. |
| 2006/0124485 A1 | 6/2006 | Kennedy |
| 2006/0217749 A1 | 9/2006 | Wilson et al. |
| 2007/0016228 A1 | 1/2007 | Salas |
| 2007/0049947 A1 | 3/2007 | Menn et al. |
| 2007/0083218 A1 | 4/2007 | A Morris |
| 2007/0118161 A1 | 5/2007 | Kennedy et al. |
| 2007/0149989 A1 | 6/2007 | Santilli et al. |
| 2007/0276417 A1 | 11/2007 | Mendes et al. |
| 2007/0282355 A1 | 12/2007 | Brown et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |

(56) References Cited

U.S. PATENT DOCUMENTS

| | | |
|---|---|---|
| 2009/0088783 A1 | 4/2009 | Kennedy et al. |
| 2009/0088786 A1 | 4/2009 | Zook et al. |
| 2009/0112233 A1 | 4/2009 | Xiao |
| 2009/0171380 A1 | 7/2009 | Whiting |
| 2009/0240266 A1 | 9/2009 | Dennis |
| 2010/0057107 A1 | 3/2010 | Sorrentino et al. |
| 2010/0082047 A1 | 4/2010 | Cosgrove et al. |
| 2010/0114131 A1 | 5/2010 | Rotunda |
| 2010/0211080 A1 | 8/2010 | Trivisani et al. |
| 2010/0274262 A1 | 10/2010 | Schulz et al. |
| 2010/0274264 A1 | 10/2010 | Schulz et al. |
| 2010/0274268 A1 | 10/2010 | Singh et al. |
| 2011/0022079 A1 | 1/2011 | Miles et al. |
| 2011/0087244 A1 | 4/2011 | Weisshaupt et al. |
| 2011/0144665 A1 | 6/2011 | Malkowski |
| 2011/0245848 A1 | 10/2011 | Rosenberg et al. |
| 2011/0295291 A1 | 12/2011 | Trivisani |
| 2012/0027765 A1 | 2/2012 | Jackson et al. |
| 2012/0074200 A1 | 3/2012 | Schmid et al. |
| 2012/0083803 A1* | 4/2012 | Patel .............. A61B 17/1285 606/157 |
| 2012/0226291 A1 | 9/2012 | Malizia et al. |
| 2012/0277765 A1 | 11/2012 | Zammataro et al. |
| 2012/0330326 A1 | 12/2012 | Creston et al. |
| 2013/0006271 A1 | 1/2013 | Vold et al. |
| 2013/0226200 A1 | 8/2013 | Kappel et al. |
| 2013/0245651 A1 | 9/2013 | Schmidt et al. |
| 2013/0245652 A1 | 9/2013 | Cosgrove et al. |
| 2013/0253535 A1 | 9/2013 | Pribanic et al. |
| 2013/0261642 A1 | 10/2013 | Willett et al. |
| 2014/0018830 A1 | 1/2014 | Shelton, IV |
| 2014/0058411 A1 | 2/2014 | Soutorine et al. |
| 2014/0207156 A1 | 7/2014 | Malkowski |
| 2014/0243862 A1 | 8/2014 | Bagaoisan et al. |
| 2014/0309677 A1 | 10/2014 | Baldwin |
| 2014/0367447 A1 | 12/2014 | Woodard, Jr. et al. |
| 2015/0066057 A1* | 3/2015 | Rockrohr .......... A61B 17/1285 606/143 |
| 2015/0105821 A1 | 4/2015 | Ward et al. |
| 2015/0136835 A1 | 5/2015 | Shelton, IV et al. |
| 2015/0190137 A1 | 7/2015 | Salas |
| 2015/0320426 A1 | 11/2015 | Cosgrove et al. |
| 2016/0151073 A1 | 6/2016 | Castro et al. |
| 2016/0174981 A1 | 6/2016 | Fago et al. |
| 2016/0213377 A1 | 7/2016 | Shankarsetty |
| 2016/0242773 A1 | 8/2016 | Sadowski et al. |
| 2016/0256157 A1 | 9/2016 | Rockrohr et al. |
| 2016/0270790 A1 | 9/2016 | Jankowski |
| 2016/0354089 A1 | 12/2016 | Whiting |
| 2017/0014135 A1 | 1/2017 | Martin et al. |
| 2017/0196620 A1 | 7/2017 | Jadhav |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0168659 A1 | 6/2018 | Bagaoisan et al. |
| 2018/0271527 A1 | 9/2018 | Shellenberger |
| 2018/0271532 A1 | 9/2018 | Shellenberger |
| 2018/0271534 A1 | 9/2018 | Shellenberger |
| 2018/0271535 A1 | 9/2018 | Shellenberger et al. |
| 2018/0271536 A1 | 9/2018 | Shellenberger et al. |
| 2019/0321048 A1 | 10/2019 | Dinino et al. |
| 2021/0128159 A1 | 5/2021 | Taylor et al. |
| 2022/0047271 A1 | 2/2022 | Shellenberger |

FOREIGN PATENT DOCUMENTS

| | | |
|---|---|---|
| CN | 1846638 A | 10/2006 |
| CN | 201123827 Y | 10/2008 |
| CN | 101543418 A | 9/2009 |
| CN | 103181809 A | 7/2013 |
| CN | 103442658 A | 12/2013 |
| CN | 103549985 A | 2/2014 |
| CN | 103930054 A | 7/2014 |
| CN | 203776975 U | 8/2014 |
| CN | 104039248 A | 9/2014 |
| CN | 104367363 A | 2/2015 |
| CN | 104414701 A | 3/2015 |
| CN | 105054989 A | 11/2015 |
| CN | 105078536 A | 11/2015 |
| CN | 204765787 U | 11/2015 |
| CN | 105816217 A | 8/2016 |
| CN | 106037947 A | 10/2016 |
| CN | 106264646 A | 1/2017 |
| CN | 207462143 U | 6/2018 |
| CN | 110740696 A | 1/2020 |
| EP | 0086640 A2 | 8/1983 |
| EP | 0201344 A2 | 11/1986 |
| EP | 0314064 A2 | 5/1989 |
| EP | 0576835 A2 | 1/1994 |
| EP | 1233705 A2 | 8/2002 |
| EP | 0893969 B1 | 6/2005 |
| EP | 2074954 A1 | 7/2009 |
| EP | 2502578 A1 | 9/2012 |
| EP | 3493747 A1 | 6/2019 |
| EP | 3600084 A1 | 2/2020 |
| GB | 2054027 A | 2/1981 |
| GB | 2069848 A | 9/1981 |
| GB | 2353710 A | 3/2001 |
| GB | 2465560 A | 5/2010 |
| JP | 56-151034 A | 11/1981 |
| JP | 61-007818 B2 | 3/1986 |
| JP | 61-259652 A | 11/1986 |
| JP | 03-178648 A | 8/1991 |
| JP | 05-200039 A | 8/1993 |
| JP | 2002-345828 A | 12/2002 |
| JP | 2004522468 A | 7/2004 |
| JP | 2004-535236 A | 11/2004 |
| JP | 4263594 B2 | 5/2009 |
| JP | 2011-036675 A | 2/2011 |
| JP | 2011-517423 A | 6/2011 |
| JP | 2014-531250 A | 11/2014 |
| JP | 2015-043977 A | 3/2015 |
| JP | 7329038 B2 | 8/2023 |
| NO | 2015/099067 A1 | 7/2015 |
| WO | 97/38634 A1 | 10/1997 |
| WO | 01/35837 A1 | 5/2001 |
| WO | 01/37742 A2 | 5/2001 |
| WO | 2004/043225 A2 | 5/2004 |
| WO | 2005/107613 A1 | 11/2005 |
| WO | 2006/102578 A1 | 9/2006 |
| WO | 2012/075532 A1 | 6/2012 |
| WO | 2013/040467 A2 | 3/2013 |
| WO | 2016/081822 A1 | 5/2016 |
| WO | 2016/094647 A1 | 6/2016 |
| WO | 2018/027032 A1 | 2/2018 |
| WO | 2018175626 A1 | 9/2018 |
| WO | 2020/018784 A1 | 1/2020 |

OTHER PUBLICATIONS

International Search Report (ISR) (PCT Form PCT/ISA/210) dated May 31, 2018, in PCTUS2018/023593.

International Search Report and Written Opinion issued in PCT/US18/23649, dated Jun. 11, 2018.

International Search Report and Written Opinion issued in PCT/US2018/023600, dated Jun. 4, 2018.

International Search Report and Written Opinion issued in PCT/US2018/023648, dated Sep. 4, 2018.

International Search Report and Written Opinion issued in PCT/US2019/042390, dated Nov. 5, 2019.

Partial Supplementary Search Report issued in European Application No. 18771180.9, dated Dec. 2, 2020.

Partial Supplementary Search Report issued in European Application No. 18771639.4, dated Nov. 27, 2020.

Notice of Allowance in CN 201880020554.4, mailed Aug. 1, 2024, with partial machine translation.

* cited by examiner

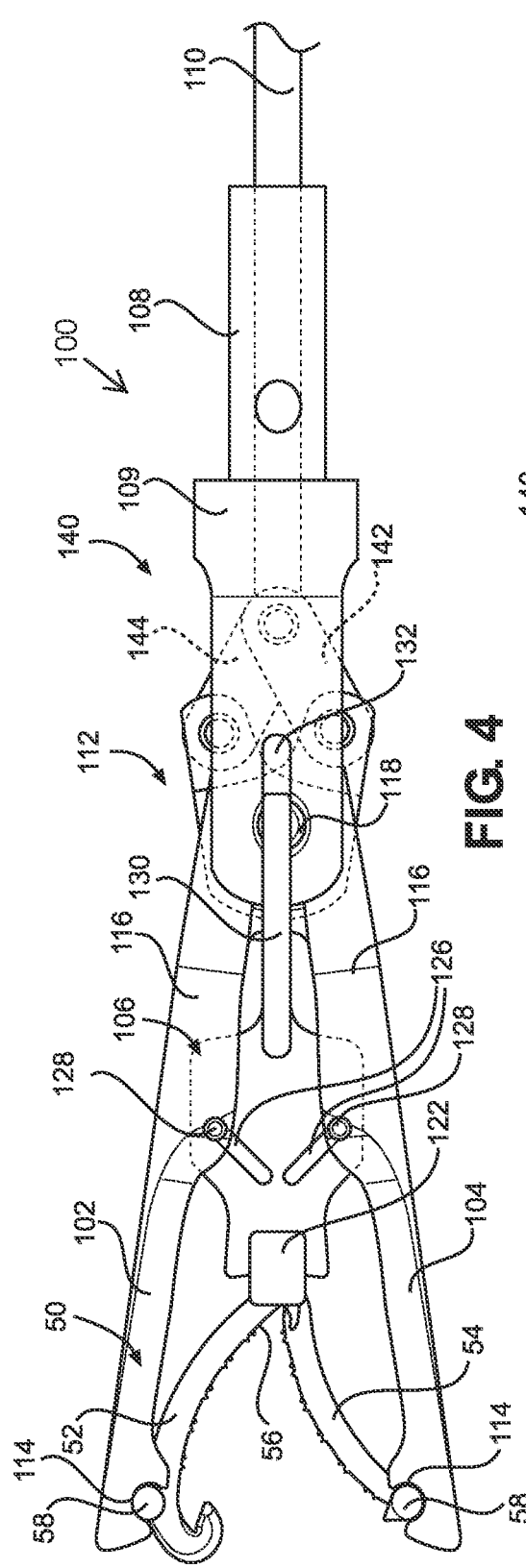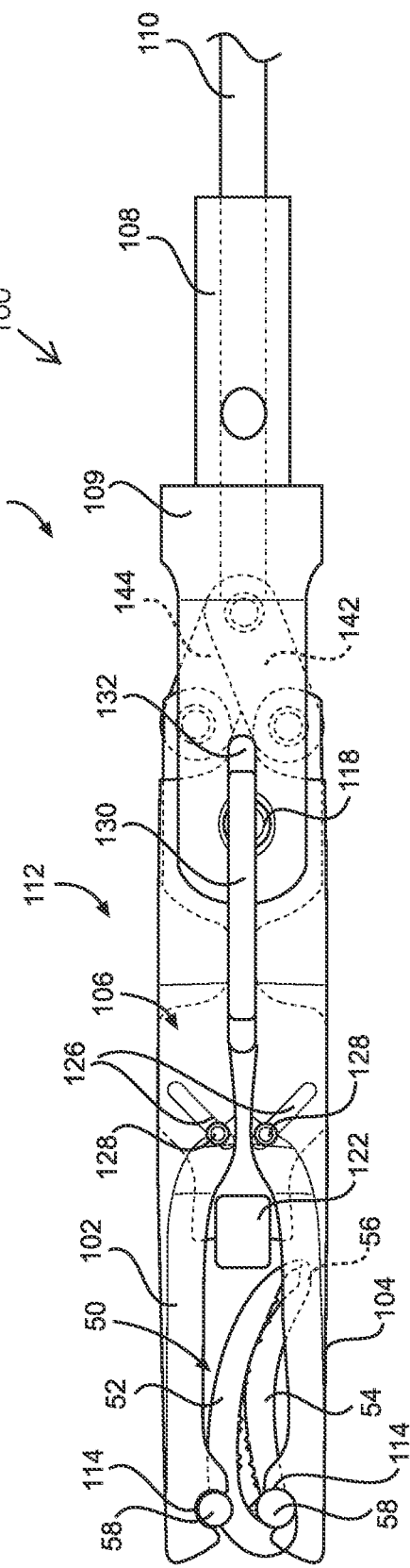

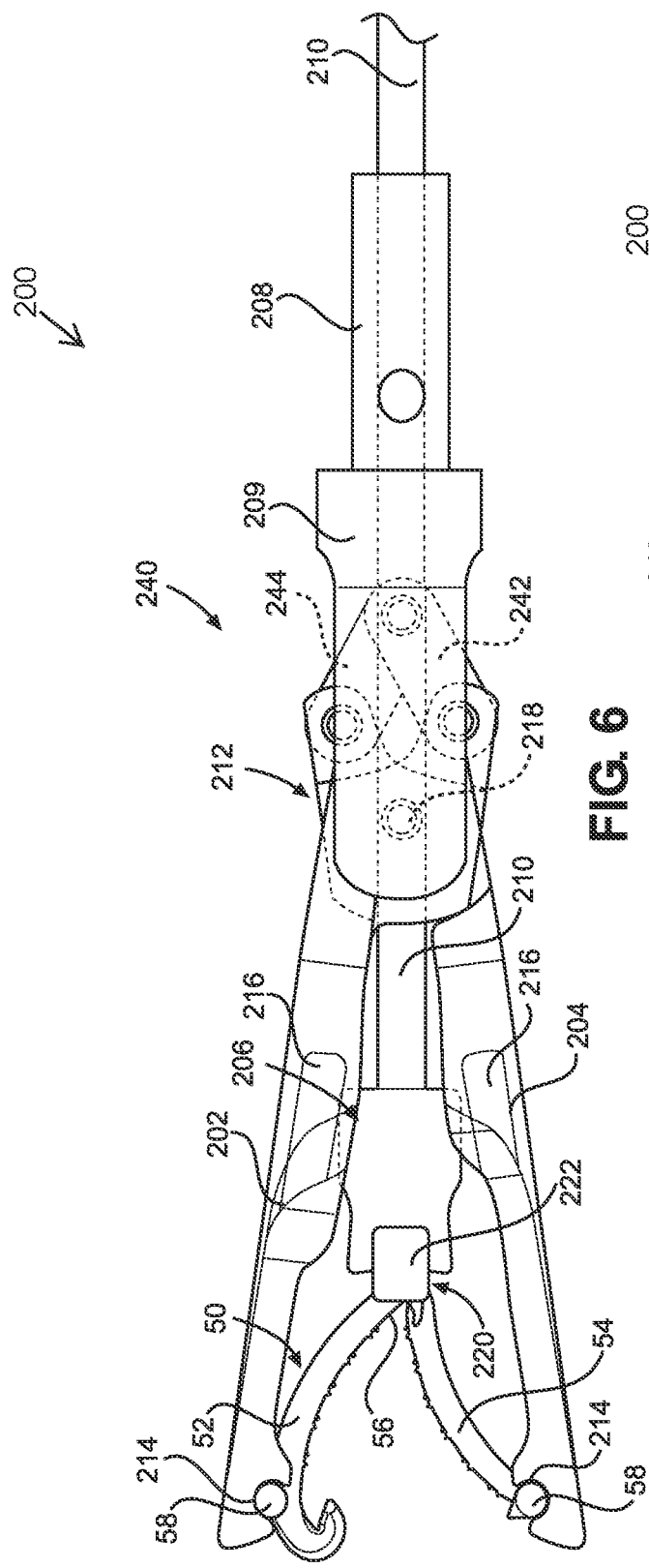
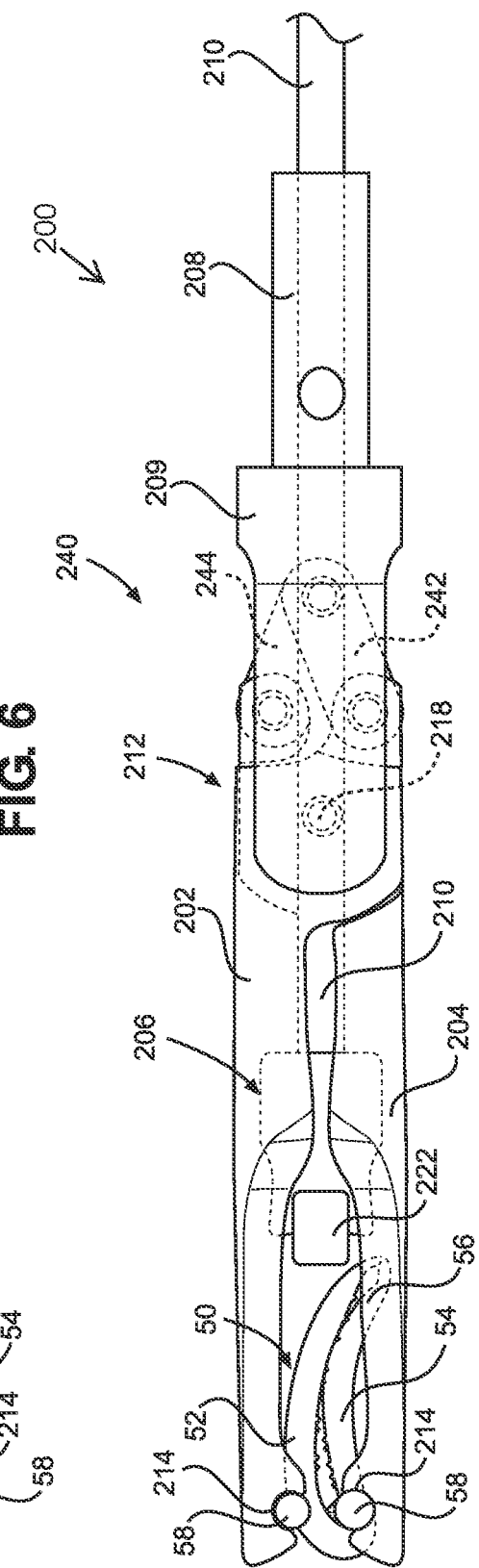

CLIP APPLIER WITH STABILIZING MEMBER

PRIORITY

This application is a continuation of International Patent Application PCT/US2019/053145 (filed Sep. 26, 2019), which claims the benefit of priority of U.S. Provisional Patent Application No. 62/737,043 (filed Sep. 26, 2018), the disclosures of which are expressly incorporated herein by reference in their entirety.

TECHNICAL FIELD

The present disclosure relates generally to clip appliers, and more particularly, to clip appliers with a stabilizing member configured to stabilize a surgical clip.

BACKGROUND

Ligation of tissue (e.g., blood vessels, lymph nodes, nerves, fallopian tubes, and cardiac tissue) is a common practice for many surgical procedures. This can be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly in endoscopic surgical procedures characterized by limited space and/or visibility. In contrast, surgical clips are relatively quick and easy to apply. Accordingly, the use of surgical clips in endoscopic and open surgical procedures has grown dramatically.

SUMMARY

The present inventor recognizes that there is a need to improve one or more features of the clip appliers, such as stability of the surgical clip in a clip applier. Surgical clips are often applied by clip appliers with a pair of opposing jaws. Currently available clip appliers often secure the clip with two points of contact, for example, the opposing jaws may engage bosses on distal ends of the surgical clip. However, the two points of contact do not provide sufficient stability to the surgical clip, which may cause the surgical clip to become misaligned relative to the clip applier during a surgical procedure, or even fall out. The disclosed methods and systems are directed to mitigating or overcoming one or more of the problems set forth above and/or other problems in the prior art.

A first aspect of the present invention is directed to a clip applier configured to apply a surgical clip to tissue. The clip applier may include first and second jaw members configured to engage the surgical clip, an actuating member configured to pivot at least one of the first and second jaw members between an open configuration and a closed configuration, and a stabilizing member configured to engage the surgical clip. The stabilizing member may be configured to move longitudinally with respect to the clip applier from a distal position at least partially between the first and second jaw members to a proximal position at least partially between the first and second jaw members. Movement of the stabilizing member between the distal position and the proximal position may be actuated by at least one of the first jaw member, the second jaw member, and the actuating member.

In some embodiments, the stabilizing member may be configured to disengage the surgical clip when the stabilizing member is in the proximal position. In some embodiments, the stabilizing member may have at least one slot, and at least one of the first and second jaw members may have a pin received in a slot of the at least one slot, where the pin slides along the slot to actuate the stabilizing member. In some embodiments, the at least one slot may be angled relative to a longitudinal axis of the clip applier. In some embodiments, the at least one slot may include a first slot and a second slot, and each of the first and second jaw members may include a pin. In some embodiments, the actuating member may be directly attached to a proximal portion of the stabilizing member. In some embodiments, the stabilizing member may be configured to stabilize a proximal portion of the surgical clip in a lateral direction. In some embodiments, the stabilizing member may include first and second walls or protrusions on a distal portion configured to receive the proximal portion of the surgical clip therebetween. In some embodiments, the first jaw member may have a first inner channel, and the second jaw member may have a second inner channel, where the stabilizing member may be received in the first and second inner channels in the closed configuration. In some embodiments, the clip applier may have a linkage connecting the actuating member and the first and second jaw members. In some embodiments, the actuating member may include an actuating rod. In some embodiments, the first jaw member may be configured to engage a distal portion of a first leg member of the surgical clip, the second jaw member may be configured to engage a distal portion of a second leg member of the surgical clip, and the stabilizing member may be configured to engage a proximal portion of the surgical clip. In some embodiments, the stabilizing member is constrained to longitudinal movement between the distal and proximal positions. In some embodiments, actuating the actuating member, pivoting the at least one of the first and second jaw members to the closed configuration, and moving the stabilizing member from the distal position to the proximal position are performed simultaneously.

A second aspect of the present invention is directed to a method of applying a surgical clip with a clip applier. The method may include receiving the surgical clip between first and second jaw members of the clip applier, and engaging the proximal portion of the surgical clip with a stabilizing member in a distal position at least partially between the first and second jaw members. The method may further include moving an actuating member to pivot at least one of the first and second jaws members toward a closed configuration to close the surgical clip, and moving the stabilizing member from the distal position to a proximal position by actuation of at least one of the first jaw member, the second jaw member, and the actuating member.

In some embodiments, the method may further include disengaging the surgical clip from the stabilizing member when the stabilizing member is in the proximal position. In some embodiments, the method may further include sliding a pin of at least one of the first and second jaw members through a slot in the stabilizing member to actuate the stabilizing member. In some embodiments, moving the stabilizing member may be actuated through a direct connection with the actuating rod. In some embodiments, the method may further include receiving the proximal portion of the surgical clip between first and second walls of the stabilizing member to stabilize the proximal portion of the surgical clip. In some embodiments, the method may further include actuating a linkage with the actuating member to pivot at least one of the first and second jaw members. In some embodiments, the method may further include receiving the stabilizing member in a first inner channel of the first jaw member and a second inner channel of the second jaw member in the closed configuration. In some embodiments, the method may further include engaging a distal portion of a first leg member with the first jaw member and a distal portion of a second leg member with the second jaw member. In some embodiments, moving the stabilizing member is constrained to longitudinal movement between the distal and proximal positions. In some embodiments, moving the actuating member, pivoting the at least one of the first and second jaw members to the closed configuration, and moving the stabilizing member from the distal position to the proximal position are performed simultaneously.

BRIEF DESCRIPTION OF THE DRAWINGS

In order that the disclosure may be readily understood, aspects of this disclosure are illustrated by way of examples in the accompanying drawings.

FIG. 4 illustrates a side view of the first exemplary embodiment of FIGS. 2-3 in an open configuration with a surgical clip.

FIG. 5 illustrates aside view of the first exemplary embodiment of FIGS. 2-4 in a closed configuration with the surgical clip.

FIG. 6 illustrates a side view of a second exemplary embodiment of a distal end effector of the manual clip applier of FIG. 1 in an open configuration with a surgical clip.

FIG. 7 illustrates aside view of the second exemplary embodiment of FIG. 6 in a closed configuration with the surgical clip.

The same or similar reference numbers are used in the drawings and the following detailed description to refer to the same or similar parts.

DETAILED DESCRIPTION

Figure 1:
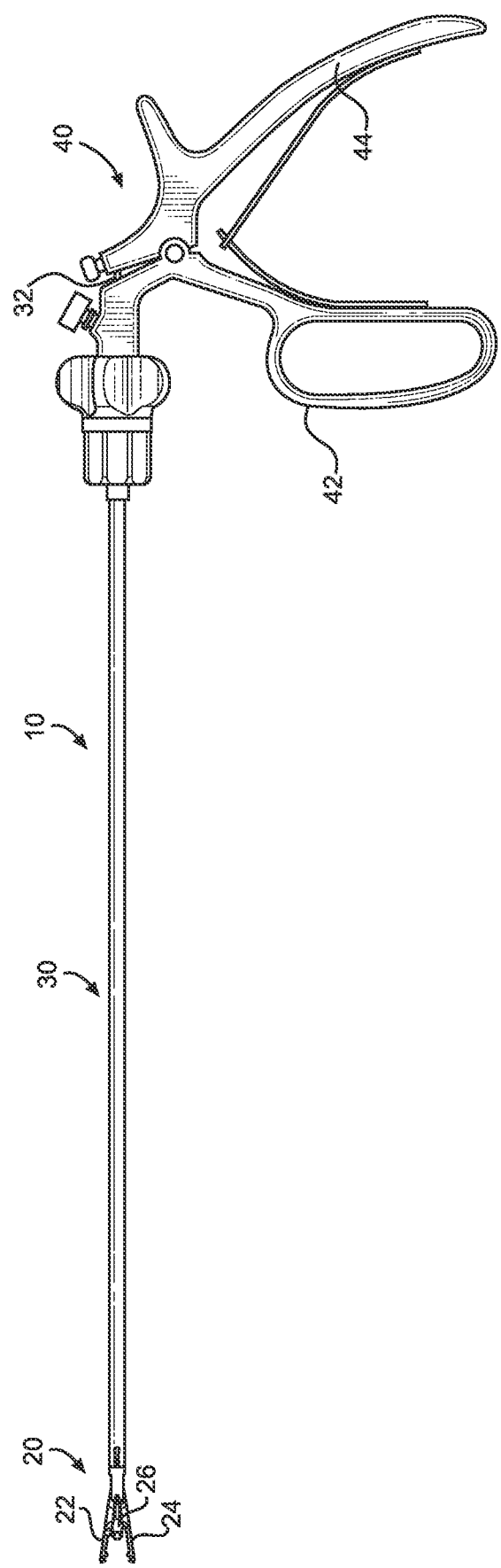
FIG. 1 illustrates a manual clip applier of the present disclosure.
Figure 2:
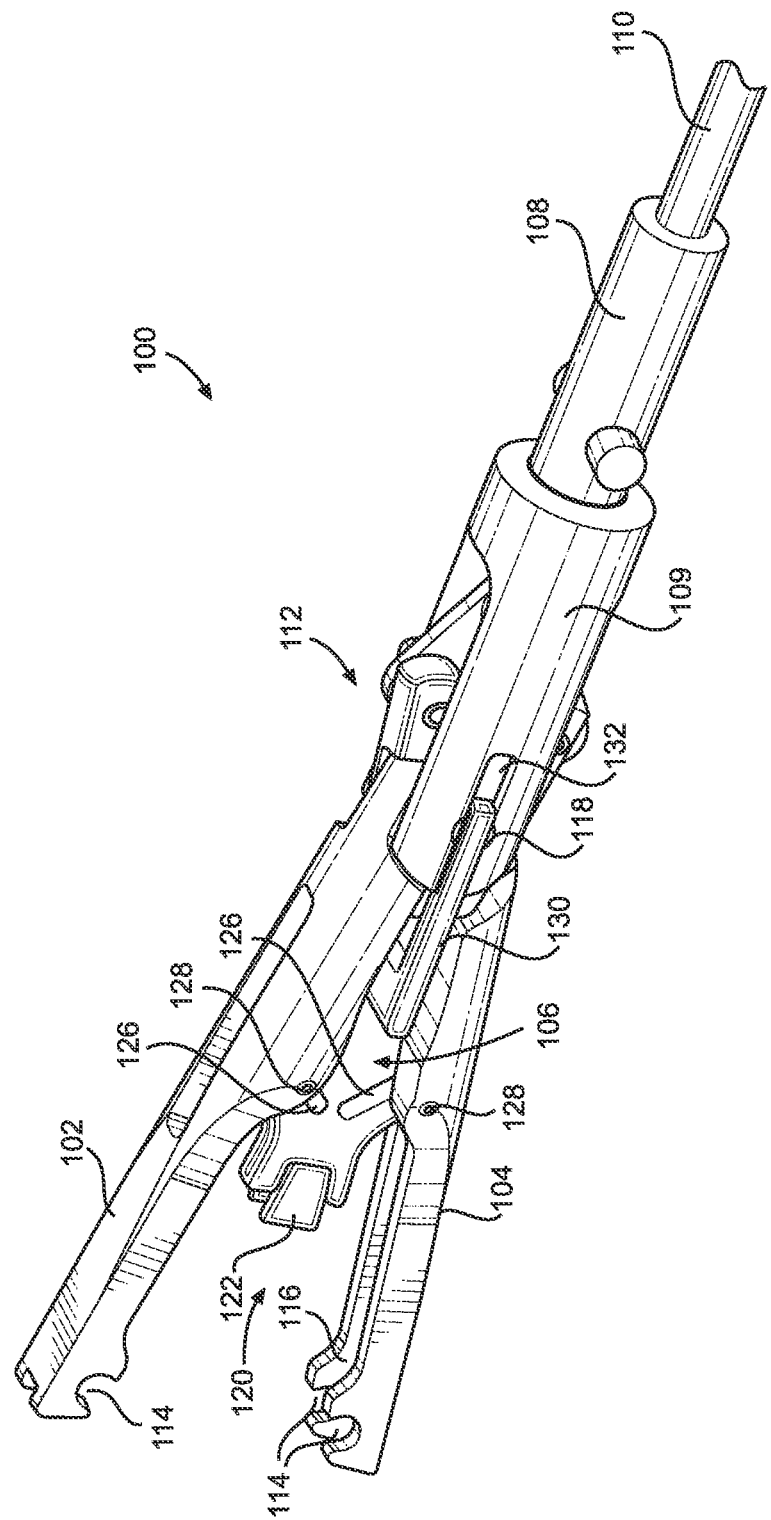
FIG. 2 illustrates a first perspective view of a first exemplary embodiment of a distal end effector of the manual clip applier of FIG. 1.
Figure 3:
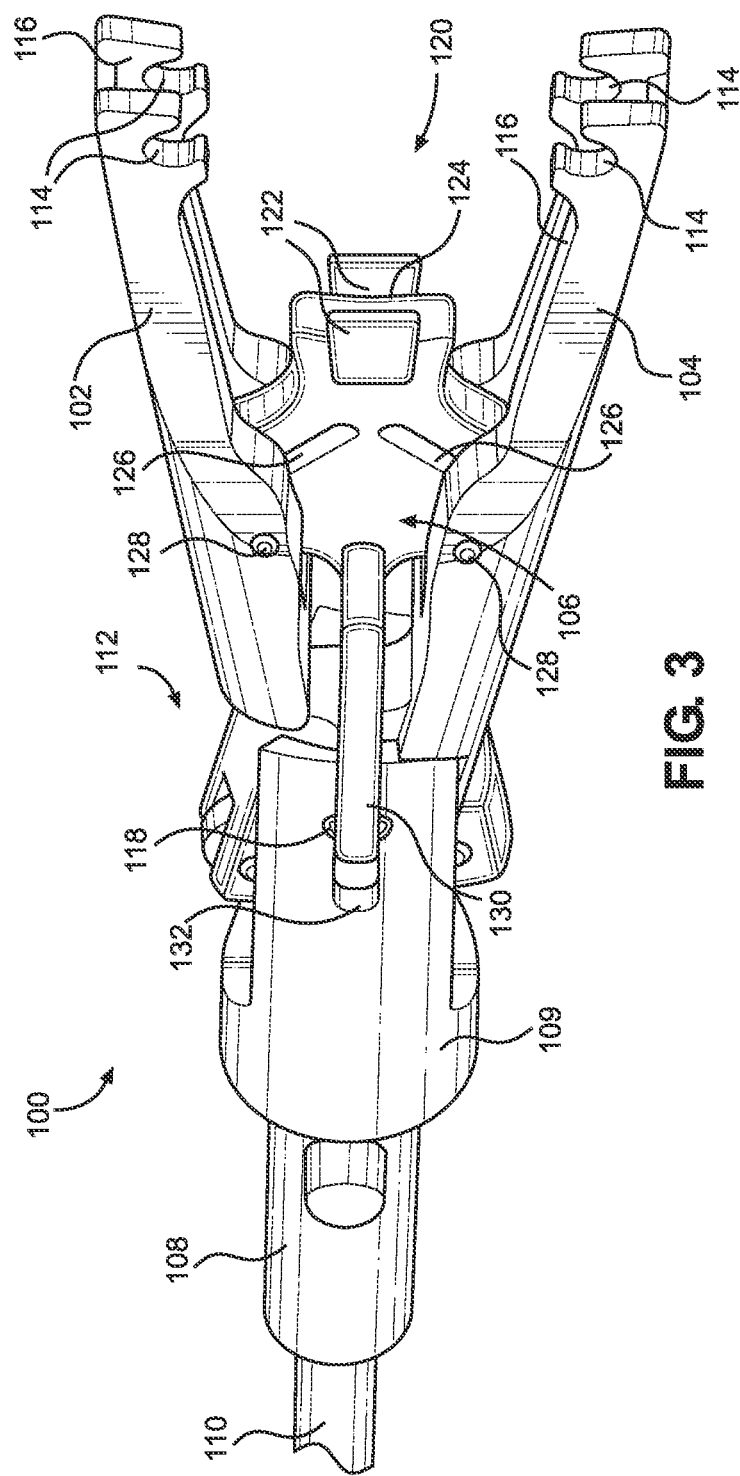
FIG. 3 illustrates a second perspective view of the first exemplary embodiment of FIG. 2.

The invention will now be described with reference to the figures, in which like reference numerals refer to like parts throughout. In accordance with conventional practice, as used herein, and unless otherwise indicated herein, the term "proximal" refers to the relative positioning of a device or its component generally closer to the medical personnel handling or manipulating the device as it is intended to be used, and the term "distal" refers to the relative positioning of a device or its component further from the medical personnel handling or manipulating the device as it is intended to be used. The term "vertical" with reference to the clip applier of a component refers to a relative direction of the clip applier parallel or along a plane extending evenly through both jaw members or similarly to the component. The term "longitudinal" relative to the clip applier or a component refers to a relative direction along a long axis or length of the clip applier or the component. The term "lateral" relative to the clip applier or a component refers to a relative direction parallel or along a plane extending perpendicularly between the first and second jaw members or similarly to the component.

The present invention is generally directed to a manual clip applier configured to increase stability of surgical clips during a medical procedure. The manual clip applier may include a stabilizing member disposed between first and second jaw members. The stabilizing member and the first and second jaw members may provide at least three points of contact with the surgical clip to prevent relative movement of the surgical clip during the medical procedure. The stabilizing member may have vertical walls extending from a distal portion configured to receive a proximal portion of the surgical clip and laterally stabilize the surgical clip. The vertical walls may extend from a distal portion of the stabilizing member on opposing sides to reduce lateral movement of the surgical clip. The vertical walls may stabilize the surgical clip while the surgical clip is loaded, manipulated, and/or delivered to tissue (e.g., to ligate a blood vessel), preventing the surgical clip from fish-tailing. The stabilizing member may further have lateral protrusions extending between the vertical walls and being configured to reduce vertical movement.

The stabilizing member may be configured to move longitudinally between a first, distal position and a second, proximal position to allow the stabilizing member to apply a sufficient distal stabilizing force when the surgical clip is received between the first and second jaw members of the clip applier during front-loading of the manual surgical clip from a clip cartridge. The stabilizing member may longitudinally retract to the proximal position during compression of the surgical clip, so the stabilizing member does not interfere with elongation of the surgical clip during compression and/or release of the surgical clip after being closed/latched onto the tissue. The movement of the stabilizing member may be directly actuated by at least one of the first jaw member, the second jaw member, and an actuating member (e.g. an actuating rod) that actuates the first and second jaw members. Thus, the stabilizing member is actuated independently of the surgical clip, such that the stabilizing member moves longitudinally when the clip applier is not loaded and in the absence of a surgical clip. The actuation of the stabilizing member may be based on movement of at least one of the first jaw member, the second jaw member, and the actuating member, such that the stabilizing member moves between proximal and distal positions as the first and second jaw members open and close. For example, in some embodiments, the stabilizing member may include angled slots that receive pins from the first and second jaw members. The angled slots may directly cause the stabilizing member to retract while the jaw members pivot closed and the stabilizing member to advance while the jaw members pivot open. In some embodiments, a distal end of the actuating member may be directly connected to a proximal end of the stabilizing member, such that retraction of the actuating member directly causes the stabilizing member to retract as the jaw members close and advancement of the actuating member directly causes the stabilizing member to advance as the jaw members open. In some embodiments, a distal end of the actuating member may be integrally attached to a proximal end of the stabilizing member. Thus, moving/retracting the actuating member, pivoting at least one of the first and second jaw members toward a closed configuration, and moving the stabilizing member from the distal position to the proximal position may be performed simultaneously in the absence of a surgical clip. The opposite movements may be performed simultaneously as the first and second jaw members pivot toward an open configuration, for example, to load a second surgical clip.

FIG. 1 illustrates a manual clip applier 10 according to the present disclosure. The clip applier 10 may include a distal end effector including a jaw mechanism 20 at a distal end of an elongated shaft 30 and a handle mechanism 40 at a proximal end of the elongated shaft 30. The jaw mechanism 20 may include a first jaw member 22, a second jaw member 24, and a stabilizing member 26 between the first and second jaw members 22, 24. The jaw mechanism 20 may be actuated by the handle mechanism 40 via an actuating member 32 extending through the elongated shaft 30. The handle mechanism 40 may include a first handle member 42 and a second handle member 44. For example, a proximal end of the elongated shaft 30 may be attached to the first handle member 42, and a proximal end of the actuating member 32 may be attached to the second handle member 44, such that relative movement or pivoting of the handle members 42, 44 may cause relative movement of the actuating member 32 to actuate the jaw mechanism 20. In some embodiments, the jaw mechanism 20 may be releasably attached to the handle mechanism 40 and the elongated shaft 30 for cleaning purposes. For example, a pin on the distal end effector may be received in a slot on the distal end of the elongated shaft 30. The actuation of the first jaw member 22, the second jaw member 24, and the stabilizing member 26 is discussed in the exemplary embodiments herein.

FIGS. 2-5 illustrate a first embodiment 100 of the distal end effector of the manual clip applier 10 of FIG. 1. The clip applier 100 may be configured to apply a surgical clip 50 (as illustrated in FIGS. 4-5). The clip applier 100 may include a first jaw member 102, a second jaw member 104, a stabilizing member 106, a shaft 108, and a handle mechanism (as illustrated in FIG. 1). Actuation of the handle mechanism may retract and/or advance an actuating member (e.g., an actuating rod) 110 through the shaft 108 to cause the first and second jaw members 102, 104 to pivot between an open configuration (e.g., FIG. 4) and a closed configuration (e.g., FIG. 5). The first and second jaw members 102, 104 may thus compress the surgical clip 50 by pivoting first and second leg members 52, 54 about a hinge portion 56.

The first and second jaw members 102, 104 may be pivotally coupled at a hinge mechanism 112 having a pivot pin 118 on a distal portion 109 of the shaft 108. The first and second jaw members 102, 104 may receive the surgical clip 50 between the first and second jaw members 102, 104, and the first and second jaw members 102, 104 may stabilize the surgical clip 50 at points of contact on distal portions of the first and second leg members 52, 54. For example, as illustrated in FIGS. 2-5, the first and second jaw members 102, 104 may have distal portions with one or more recesses 114 that receive one or more bosses 58 on distal portions of the first and second leg members 52, 54. Each of the first and second jaw members 102, 104 may further include a longitudinal channel 116 configured to receive a portion of the surgical clip 50 and/or the stabilizing member 106.

The stabilizing member 106 may be received between the first and second jaw members 102, 104 to provide additional stability to the surgical clip 50. The stabilizing member 106 may include an elongated body having a distal portion 120 that receives and/or engages the proximal portion (e.g., the hinge portion 56) of the surgical clip 50. The distal portion 120 may include vertical walls or protrusions 122 extending from the distal portion 120 of the elongated body on opposing sides of the stabilizing member 106. For example, the vertical walls 122 may be integrated, welded, and/or secured to opposing lateral sides of the elongated body of the stability member 106, such that the width defined by the vertical walls 122 may be wider than the width of the remaining length of the stabilizing member 106. The vertical walls 122 may define a channel 124 therebetween configured to receive the proximal portion (e.g., the hinge portion 56) of the surgical clip 50, reducing lateral movement of the surgical clip 50. The vertical walls 122 may be substantially parallel, and may not extend the entire height of the distal portion 120. The distal portion 120 may further include lateral protrusions (not shown) extending laterally between the vertical walls 122 to engage the proximal portion of the surgical clip 50. Thus, the distal portion 120 may receive, grip, and/or stabilize the surgical clip 50 in a lateral and/or vertical direction when positioned between the first and second jaw members 102, 104. Embodiments of the distal portion 120 of the stabilizing member 106 are further disclosed in U.S. Pat. Pub. No. 2018/0271534, the disclosure of which is expressly incorporated herein in its entirety.

The stabilizing member 106 may be positioned symmetrically between the first and second jaw members 102, 104. The positioning of the stabilizing member 106 may allow a user to pick up the surgical clip 50 from a clip cartridge (not shown) with the clip applier 100 in either of two opposite orientations. For example, the first jaw member 102 may engage either of the first leg member 52 or the second leg member 54 of the surgical clip 50, while the second jaw member 104 engages the other of the first leg member 52 and the second leg member 54. The three point engagement between the clip applier 100 and the surgical clip 50 increases the security of the surgical clip 50. Two points of contact occur on the surgical clip 50 at distal surfaces of the first and second leg members 52, 54, and a third point of contact occurs at a proximal portion of the surgical clip 50 (e.g., the hinge portion 56). The surgical clip 50 may remain positively engaged between the first and second jaw members 102, 104, despite external forces.

As illustrated in FIGS. 4-5, the first and second jaw members 102, 104 may be configured to compress the surgical clip 50 by applying opposing forces on the first and second leg members 52, 54. The clip applier 100 may be initially loaded with the surgical clip 50 from the clip cartridge (not shown), such that the first and second jaw members 102, 104 engage distal portions of the leg members 52, 54 (e.g., bosses on surgical clip engaged by recesses 114) and the hinge portion 56 is received between the vertical walls 122 of the stabilizing member 106 when the stabilizing member 106 is in a distal position. Actuation of the handle mechanism may retract the actuating member 110, which may be coupled to the first and second jaw member 102, 104 through a linkage 140 received in the distal portion 10) of the shaft 108. For example, a first link 142 may have a first end pivotally coupled to the actuating member 110 and a second end pivotally coupled to a proximal end of the first jaw member 102. A second link 144 may have a first end pivotally coupled to the actuating member 110 and a second end pivotally coupled to a proximal end of the second jaw member 104. The attachment of the linkage 140 may be proximal of the hinge mechanism 112, such that retraction of the actuating member 110 causes the first and second jaw members 102, 104 to pivot to a closed configuration. The distal portion 109 may be open and enlarged relative to a proximal portion of the shaft 108, such that the distal portion 109 may receive proximal ends of the jaw members 102, 104 that are pivoted about the pivot pin 118.

As the first and second jaw members 102, 104 pivot, the stabilizing member 106 may be configured to move longitudinally between a first, distal position at least partially between the first and second jaw members 102, 104 (e.g., FIG. 4) and a second, proximal position at least partially between the first and second jaw members 102, 104 (e.g., FIG. 5). The stabilizing member 106 may be constrained to longitudinal movement between the first and second positions. The elongated body of the stabilizing member 106 may be received in the longitudinal channels 116 of the first and/or second jaw members 102, 104 in the first and/or second positions to prevent impeding of the pivoting of the jaw members 102, 104. After compression of the surgical clip 50, the jaw members 102, 104 may pivot to the open configuration thus returning stabilizing member 106 to the first, distal position to engage a second surgical clip 50 from a cartridge.

As illustrated in the FIGS. 4-5, the movement of the stabilizing member 106 may be directly actuated by the pivoting of the jaw members 102, 104. For example, the stabilizing member 106 may include one or more slots 126 slideably receiving a pin 128 of one or more the jaw members 102, 104. Thus, the pins 128 may be in a proximal position in the slots 126 when the jaw members 102, 104 are in an open configuration and the stabilizing member 106 is in the distal position to engage the surgical clip 50 (e.g., FIG. 4). As the jaw members 102, 104 pivot to the closed position, the pins 128 may slide through the slots 126 to a distal position when the jaw members 102, 104 are in a closed configuration and the stabilizing member 106 is in the proximal position to disengage the surgical clip 50 (e.g., FIG. 5). As further illustrated in FIGS. 4-5, stabilizing member 106 may include first and second slots 126 to receive a pin 128 from each of the first and second jaw members 102, 104 to allow pivoting of both first and second jaw members 102, 104 relative to the shaft 108. However, in other embodiments (not shown), the stabilizing member 106 may include a single slot 126 when pivoting only one of the first and second jaw members 102, 104 is desired. The slots 126 may be linearly angled relative to the longitudinal axis of the clip applier 100, such that the pins 128 simultaneously move longitudinally and vertically through the slots 126. Thus, the stabilizing member 106 retracts longitudinally while the first and second jaw members 102, 104 pivot toward each other. The slots 126 are preferably linear/straight, but can be curved to provide the simultaneous pivoting of the jaw members 102, 104 and longitudinal movement of the stabilizing member 106.

The stabilizing member 106 may be vertically and/or laterally stabilized with an extension 130. The extension 130 may be integral to the stabilizing member 106, extend proximally, and engage a longitudinal slot 132 in the distal portion 109 of the shaft 108. The extension 130 may longitudinally slide through the longitudinal slot 132 during actuation, while preventing lateral and/or vertical play/movement of the extension 130. Thus, the stabilizing member 106 may move longitudinally relative to the pins 128 of the first and second jaw members 102, 104 without any substantial rotation or play.

FIGS. 6-7 illustrates a second embodiment 200 of the distal end effector of the manual clip applier 10 of FIG. 1. The clip applier 200 may be configured to apply the surgical clip 50. The clip applier 200 may include a first jaw member 202, a second jaw member 204, a stabilizing member 206, a shaft 208, and a handle mechanism (as illustrated in FIG. 1). Actuation of the handle mechanism may retract and/or advance an actuating member (e.g., an actuating rod) 210 through the shaft 208 to cause the first and second jaw members 202, 204 to pivot between an open configuration (e.g., FIG. 6) and a closed configuration (e.g., FIG. 7). The first and second jaw members 202, 204 may thus compress the surgical clip 50 by pivoting the first and second leg members 52, 54 about the hinge portion 56.

The first and second jaw members 202, 204 may be pivotally coupled at a hinge mechanism 212 having a pivot pin 218 on a distal portion 209 of the shaft 208. The first and second jaw members 202, 204 may receive the surgical clip 50 between the first and second jaw members 202, 204, and the first and second jaw members 202, 204 may stabilize the surgical clip 50 at points of contact on distal portions of the first and second leg members 52, 54. For example, as similarly illustrated in FIGS. 2-5, the first and second jaw members 202, 204 may have distal portions with one or more recesses 214 that receive one or more bosses 58 on distal portions of the first and second leg members 52, 54. Each of the first and second jaw members 202, 204 may further include a longitudinal channel 216 configured to receive a portion of the surgical clip 50 and/or the stabilizing member 206.

The stabilizing member 206 may be received between the first and second jaw members 202, 204 to provide additional stability to the surgical clip 50. The stabilizing member 206 may include an elongated body having a distal portion that receives and/or engages the proximal portion (e.g., a hinge portion 16) of the surgical clip 50. The distal portion 220 may include vertical walls or protrusions 222 extending from the distal portion 220 on opposing sides of the stabilizing member 206. The vertical walls 222 may define a channel 224 therebetween configured to receive the proximal portion (e.g., the hinge portion 56) of the surgical clip 50, reducing lateral movement of the surgical clip 50. For example, the vertical walls 222 may be integrated, welded, and/or secured to opposing lateral sides of the elongated body of the stability member 206, such that the width defined by the vertical walls 222 may be wider than the width of the remaining length of the stabilizing member 206. The vertical walls 222 may be substantially parallel, and may not extend the entire height of the distal portion 220. The distal portion 220 may further include lateral protrusions (not shown) extending laterally between the vertical walls 222 to engage the proximal portion of the surgical clip 50. Thus, the distal portion 220 may receive, grip, and/or stabilize the surgical clip 50 in a lateral and/or vertical direction when positioned between the first and second jaw members 202, 204, as discussed above.

The stabilizing member 206 may be positioned symmetrically between the first and second jaw members 202, 204. The positioning of the stabilizing member 206 may allow a user to pick up the surgical clip 50 from a clip cartridge (not shown) with the clip applier 200 in either of two opposite orientations. For example, the first jaw member 202 may engage either of the first leg member 52 or the second leg member 54 of the surgical clip 50, while the second jaw member 204 engages the other of the first leg member 52 and the second leg member 54. The three point engagement between the clip applier 200 and the surgical clip 50 increases the security of the surgical clip 50. Two points of contact occur on the surgical clip 50 at distal surfaces of the first and second leg members 52, 54, and a third point of contact occurs at a proximal portion of the surgical clip 50 (e.g., the hinge portion 56). The surgical clip 50 may remain positively engaged between the first and second jaw members 202, 204, despite external forces.

As illustrated in FIGS. 6-7, the first and second jaw members 202, 204 may be configured to compress the surgical clip 50 by applying opposing forces on the first and second leg members 52, 54. The clip applier 200 may be initially loaded with the surgical clip 50 from the clip cartridge (not shown), such that the first and second jaw members 102, 104 engage distal portions of the leg members 52, 54 (e.g., with recesses 214) and the hinge portion 56 is received between the vertical walls 222 of the stabilizing member 106. Actuation of the handle mechanism may retract the actuating member 210, which may be coupled to the first and second jaw member 202, 204 through a linkage 240. For example, a first link 242 may have a first end pivotally coupled to the actuating member 210 and a second end pivotally coupled to a proximal end of the first jaw member 202. A second link 244 may have a first end pivotally coupled to the actuating member 210 and a second end pivotally coupled to a proximal end of the second jaw member 204. The attachment of the linkage 240 may be proximal of the hinge mechanism 212, such that retraction of the actuating member 210 causes the first and second jaw members 202, 204 to close.

As the first and second jaw members 202, 204 pivot, the stabilizing member 206 may be configured to move longitudinally between a first, distal position at least partially between the first and second jaw members 202, 204 (e.g., FIG. 6) and a second, proximal position at least partially between the first and second jaw members 202, 204 (e.g., FIG. 7). The stabilizing member 206 may be constrained to longitudinal movement between the first and second positions. The stabilizing member 206 may be received in the longitudinal channels 216 of the first and/or second jaw members 202, 204 in the first and/or second positions to prevent impeding of the pivoting of the jaw members 202, 204. After compression of the surgical clip 50, the jaw members 202, 204 may pivot to the open configuration thus returning stabilizing member 206 to the first, distal position to engage a second surgical clip 50 from a cartridge. The clip applier 200 may have features and function similar to the clip applier 100 except when otherwise indicated.

As illustrated in FIGS. 6-7, the movement of the stabilizing member 206 may be directly actuated by the longitudinal movement of the actuating member 210. The stabilizing member 206 may be directly attached (e.g., integral) to the actuating member 210. Thus, as illustrated in FIGS. 6-7, the actuating member 210 may extend from the handle mechanism, past the linkage 240, past the pivot pin 218, and directly attach (e.g. be integrated) to the stabilizing member 206. Retraction and advancement of the actuating member 210 would therefore cause direct retraction and advancement of the stabilizing member 206.

As further illustrated in FIGS. 4-7, the first leg member 52 of the surgical clip 50 may have a concave inner surface and a hook member on a distal portion, and the second leg member 54 may include convex inner surface and a tip member on a distal portion. As the surgical clip 50 closes, the hook on the first leg member 52 may deflect around the tip member on the second leg member to secure the surgical clip 50 in a latched configuration. Due to the curvatures, the first and/or second leg members 52, 54 may straighten and/or elongate during the closing and/or latching process. Thus, retraction of the stabilizing member 106, 206 as discussed herein prevents interference with the closing and/or latching of the surgical clip 50. The retraction of the stabilizing member 106, 206 also facilitates release of the surgical clip 50 after closing and/or latching of the surgical clip 50.

The surgical clip 50 may be made of any suitable size and may be applied to any number of tissues, such as blood vessels, lymph nodes, nerves, fallopian tubes, or cardiac tissue. The surgical clip 50 may be constructed from any suitable biocompatible material, such as metals and polymers. In some embodiments, the surgical clip 50 consists of a one-piece integral polymeric body formed from a suitable strong biocompatible engineering plastic such as the type commonly used for surgical implants. Exemplary materials include homopolymer or co-polymer polyacetal, polyethylene terephthalate (PET), polybutylene terephthalate (PBT), polyoxymethylene, or other thermoplastic materials having similar properties that can be injection-molded, extruded, or otherwise processed into like articles. Embodiments of the surgical clip 50 are further disclosed in U.S. Pat. No. 4,834,096, the disclosure of which is incorporated herein by reference. Embodiments of a cartridge containing the surgical clip 50 are further disclosed in U.S. Pat. No. 6,880,699, the disclosure of which is incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clip applier configured to apply a surgical clip, the clip applier comprising:
   first and second jaw members configured to engage the surgical clip;
   an actuating member configured to pivot at least one of the first and second jaw members between an open configuration and a closed configuration;
   a stabilizing member configured to engage the surgical clip, the stabilizing member being configured to move longitudinally with respect to the clip applier from a distal position at least partially between the first and second jaw members to a proximal position at least partially between the first and second jaw members; and
   at least one pin connecting the stabilizing member to the first jaw member and/or the second jaw member,
   wherein the at least one pin is configured to actuate movement of the stabilizing member between the distal position and the proximal position, such that movement of the stabilizing member is actuated by pivoting the at least one of the first and second jaw members between the open configuration and the closed configuration.

2. The clip applier of claim 1, wherein the stabilizing member is configured to disengage the surgical clip when the stabilizing member is in the proximal position.

3. The clip applier of claim 1, wherein the stabilizing member comprises at least one slot, the at least one pin is received in the at least one slot, and each pin of the at least one pin slides along a respective slot of the at least one slot to actuate the stabilizing member.

4. The clip applier of claim 3, wherein the at least one slot is angled relative to a longitudinal axis of the clip applier.

5. The clip applier of claim 3, wherein the at least one slot includes a first slot and a second slot, and the at least one pin includes a pin on each of the first and second jaw members.

6. The clip applier of claim 1, wherein the stabilizing member is configured to stabilize a proximal portion of the surgical clip in a lateral direction.

7. The clip applier of claim 1, wherein the stabilizing member includes first and second walls on a distal portion configured to receive a proximal portion of the surgical clip therebetween.

8. The clip applier of claim 1, wherein the first jaw member comprises a first inner channel, the second jaw member comprises a second inner channel, and the stabilizing member is received in the first and second inner channels in the closed configuration.

9. The clip applier of claim 1, further comprising a linkage connecting the actuating member and the first and second jaw member.

10. The clip applier of claim 1, wherein the actuating member comprises an actuating rod.

11. The clip applier of claim 1, wherein the first jaw member is configured to engage a distal portion of a first leg member of the surgical clip, the second jaw member is configured to engage a distal portion of a second leg member of the surgical clip, and the stabilizing member is configured to engage a proximal portion of the surgical clip.

12. The clip applier of claim 1, wherein the stabilizing member is constrained to longitudinal movement between the distal and proximal positions.

13. The clip applier of claim 1, wherein actuating the actuating member, pivoting the at least one of the first and second jaw members to the closed configuration, and moving the stabilizing member from the distal position to the proximal position are performed simultaneously.

14. A method of applying a surgical clip with a clip applier, the method comprising:
receiving the surgical clip between first and second jaw members of the clip applier;
engaging a proximal portion of the surgical clip with a stabilizing member in a distal position at least partially between the first and second jaw members;
moving an actuating member to pivot at least one of the first and second jaw members toward a closed configuration to close the surgical clip; and
moving the stabilizing member from the distal position to a proximal position at least partially between the first and second jaw members by actuation of the stabilizing member by sliding a pin of at least one of the first and second jaw members through a slot in the stabilizing member, such that pivoting the at least one of the first and second jaw members toward the closed configuration actuates movement of the stabilizing member toward the proximal direction.

15. The method of claim 14, further comprising disengaging the surgical clip from the stabilizing member when the stabilizing member is in the proximal position.

16. The method of claim 14, further comprising receiving the proximal portion of the surgical clip between first and second walls of the stabilizing member to stabilize the proximal portion of the surgical clip.

17. The method of claim 14, further comprising actuating a linkage with the actuating member to pivot at least one of the first and second jaw members.

18. The method of claim 14, further comprising receiving the stabilizing member in a first inner channel of the first jaw member and a second inner channel of the second jaw member in the closed configuration.

19. The method of claim 14, further comprising engaging a distal portion of a first leg member with the first jaw member and a distal portion of a second leg member with the second jaw member.

20. The method of claim 14, wherein moving the stabilizing member is constrained to longitudinal movement between the distal and proximal positions.

21. The method of claim 14, wherein moving the actuating member, pivoting the at least one of the first and second jaw members to the closed configuration, and moving the stabilizing member from the distal position to the proximal position are performed simultaneously.

* * * * *